US009820950B2

(12) United States Patent
Miller et al.

(10) Patent No.: US 9,820,950 B2
(45) Date of Patent: *Nov. 21, 2017

(54) SYSTEMS AND METHODS FOR FEEDING SUGAR ALCOHOL TO RUMINANTS DURING PERIODS OF HEAT STRESS

(71) Applicant: PURINA ANIMAL NUTRITION LLC, Shoreview, MN (US)

(72) Inventors: Bill L. Miller, Labadie, MO (US); Jill A. Davidson, Washington, MO (US); Cindie M. Luhman, Webster Groves, MO (US)

(73) Assignee: PURINA ANIMAL NUTRITION LLC, Shoreview, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/255,700

(22) Filed: Sep. 2, 2016

(65) Prior Publication Data

US 2016/0367495 A1  Dec. 22, 2016

Related U.S. Application Data

(63) Continuation of application No. 14/727,304, filed on Jun. 1, 2015, now Pat. No. 9,456,622, which is a continuation of application No. 14/158,209, filed on Jan. 17, 2014, now Pat. No. 9,044,041, which is a continuation of application No. 13/363,973, filed on Feb. 1, 2012, now Pat. No. 8,658,199.

(51) Int. Cl.

| | | |
|---|---|---|
| A23K 1/18 | (2006.01) | |
| A61K 31/047 | (2006.01) | |
| A23K 20/105 | (2016.01) | |
| A23K 20/163 | (2016.01) | |
| A23K 20/10 | (2016.01) | |
| A23K 50/10 | (2016.01) | |
| A61K 9/00 | (2006.01) | |

(52) U.S. Cl.
CPC ............ *A61K 31/047* (2013.01); *A23K 20/10* (2016.05); *A23K 20/105* (2016.05); *A23K 20/163* (2016.05); *A23K 50/10* (2016.05); *A61K 9/0068* (2013.01); *A23V 2250/64* (2013.01); *A23V 2250/642* (2013.01)

(58) Field of Classification Search
None
See application file for complete search history.

(56) References Cited

U.S. PATENT DOCUMENTS

| | | | |
|---|---|---|---|
| 2,876,157 A | 3/1959 | Selden | |
| 3,338,718 A | 8/1967 | Olson et al. | |
| 3,794,732 A | 2/1974 | Raun | |
| 3,857,971 A | 12/1974 | Abdo et al. | |
| 3,928,571 A | 12/1975 | Raun | |
| 3,956,482 A | 5/1976 | Hahn et al. | |
| 3,959,493 A | 5/1976 | Baalsrud et al. | |
| 4,127,676 A | 11/1978 | Merensalmi | |
| 4,181,709 A | 1/1980 | Dannelly | |
| 4,289,784 A | 9/1981 | Bochis et al. | |
| 4,376,790 A | 3/1983 | Ames | |
| 4,704,276 A | 11/1987 | Kantor | |
| 4,735,735 A | 4/1988 | Borggrefe et al. | |
| 4,735,809 A | 4/1988 | Donovan et al. | |
| 4,876,097 A | 10/1989 | Autant et al. | |
| 4,996,067 A | 2/1991 | Kobayashi et al. | |
| 5,021,241 A | 6/1991 | Yamahira et al. | |
| 5,081,146 A | 1/1992 | Fontenot et al. | |
| 5,137,735 A | 8/1992 | Bignon | |
| 5,139,777 A | 8/1992 | Ott et al. | |
| 5,145,695 A | 9/1992 | Smith et al. | |
| 5,190,775 A | 3/1993 | Klose | |
| 5,219,596 A | 6/1993 | Smith et al. | |
| 5,236,718 A | 8/1993 | Huchette | |
| 5,244,669 A | 9/1993 | Satoh et al. | |
| 5,252,561 A | 10/1993 | Homykiewytsch et al. | |
| 5,380,525 A | 1/1995 | Leedle et al. | |
| 5,474,785 A | 12/1995 | Wright et al. | |
| 5,496,571 A | 3/1996 | Blagdon et al. | |
| 5,503,112 A | 4/1996 | Luhman et al. | |
| 5,518,730 A | 5/1996 | Fuisz | |
| 5,529,793 A | 6/1996 | Garner et al. | |
| 5,547,686 A | 8/1996 | Jenkins | |

(Continued)

FOREIGN PATENT DOCUMENTS

| | | |
|---|---|---|
| CA | 600707 | 5/1960 |
| CA | 645019 | 7/1962 |

(Continued)

OTHER PUBLICATIONS

Christensen et al. "Effect of Method of Delivery of Propylene Glycol on Plasma Metabolites of Feed-Restricted Cattle," *J. of Dairy Science*, vol. 80, pp. 563-564 (1997).
Ensminger. *Feeds & Nutrition*, pp. 520, 526, 567 (1978).
Ensminger. "Challenge Feeding," *Animal Science*, pp. 725-726, (1977).
Khalili et. al. "The Effects of Added Glycerol or Unprotected Free Fatty Acids or a Combination of the Two on Silage Intake, Milk Production, Rumen Fermentation and Diet Digestibility in Cows Given Grass Silage Based Diets," *Agricultural Food Science in Finland*; vol. 6; Nos. 5-6; pp. 349-362 (May 1997).
Remond et al. "Effects of Feeding Sorbitol on Milk Yield and Blood Characteristics in Dairy Cows in Early Lactation", or "Effet De L'addition De Sorbitol a La Ration Des Vaches Laitieres En Debut De Lactation Sur Leurs Performances et Sur Quelques Parametres Sanguins"; *Reprod Nutr. Dev.* 26 (1 B); pp. 365-366 (1986).

(Continued)

*Primary Examiner* — Jessica Worsham
(74) *Attorney, Agent, or Firm* — Dorset & Whitney LLP; Bridget M. Hayden

(57) ABSTRACT

Systems and methods provide sugar alcohol to heat stressed ruminants to improve performance. During periods of high temperature or humidity, heat stressed ruminants may exhibit decreased dry matter intake, and in response, an effective amount of sugar alcohol such as sorbitol may be provided in the ruminant diet to cause performance to increase, which may include increased milk yield, improved feed efficiency or both compared to heat stressed dairy cattle without sugar alcohol in the diet.

9 Claims, 4 Drawing Sheets

(56) References Cited

U.S. PATENT DOCUMENTS

| | | | |
|---|---|---|---|
| 5,560,919 A | 10/1996 | Morikawa et al. |
| 5,585,134 A | 12/1996 | Cummings et al. |
| 5,660,852 A | 8/1997 | McKeown et al. |
| 5,707,617 A | 1/1998 | Conrad et al. |
| 5,741,506 A | 4/1998 | Bauchart et al. |
| 5,767,080 A | 6/1998 | Beck |
| 5,807,594 A | 9/1998 | King et al. |
| 5,843,498 A | 12/1998 | Takahashi |
| 5,858,424 A | 1/1999 | Virkki et al. |
| 5,874,103 A | 2/1999 | Moore et al. |
| 5,906,842 A | 5/1999 | Sato et al. |
| 5,958,464 A | 9/1999 | Register |
| 6,106,871 A | 8/2000 | Miller |
| 6,217,915 B1 | 4/2001 | Luchansky et al. |
| 6,229,031 B1 | 5/2001 | Strohmaier et al. |
| 6,306,427 B1 | 10/2001 | Annonier et al. |
| 6,326,051 B1 | 12/2001 | Nakasugi et al. |
| 6,440,447 B1 | 8/2002 | Luhman |
| 6,521,249 B2 | 2/2003 | Block et al. |
| 6,866,861 B1 | 3/2005 | Luhman |
| 7,037,518 B2 | 5/2006 | Luhman |
| 7,371,401 B2 | 5/2008 | Miller |
| 8,110,214 B2 | 2/2012 | Porter et al. |
| 8,440,218 B2 | 5/2013 | Luhman |
| 8,591,937 B2 | 11/2013 | Porter et al. |
| 8,980,306 B2 | 3/2015 | Luhman |
| 9,241,914 B2 | 1/2016 | Luhman |
| 9,427,414 B2 | 8/2016 | Luhman |
| 9,668,983 B2 | 6/2017 | Luhman |
| 2002/0127259 A1 | 9/2002 | Orthoefer |
| 2003/0072788 A1 | 4/2003 | Luhman |
| 2004/0142065 A1 | 7/2004 | de Rodas et al. |
| 2005/0142168 A1 | 6/2005 | Porter et al. |
| 2006/0057274 A1 | 3/2006 | Miller |
| 2006/0088576 A1 | 4/2006 | Luhman |
| 2008/0146520 A1 | 6/2008 | Block et al. |
| 2009/0028995 A1 | 1/2009 | Miller |
| 2012/0195998 A1 | 8/2012 | Porter et al. |
| 2017/0042831 A1 | 2/2017 | Luhman |

FOREIGN PATENT DOCUMENTS

| | | |
|---|---|---|
| CA | 2330091 | 7/2002 |
| EP | 0998853 B1 | 5/2000 |
| FR | 2469131 | 5/1981 |
| GB | 838766 | 6/1960 |
| GB | 2159690 | 11/1985 |
| WO | 93/21782 | 11/1993 |
| WO | 97/33488 A1 | 9/1997 |
| WO | 00/78160 | 12/2000 |
| WO | 01/67879 | 9/2001 |
| WO | 03/037102 A2 | 5/2003 |
| WO | 03/045401 A1 | 6/2003 |
| WO | 03/090696 A2 | 11/2003 |

OTHER PUBLICATIONS

Makinen et al. "A Polyol Mixture in the Diet of Dairy Cows," *Nutrition Reports International*, vol. 23, No. 6, pp. 1077-1088 (Jun. 1981).

Choung et al. "The Effects of Abomasal Infusions of Casein or Soya-Bean-Protein Isolate on the Milk Production of Dairy Cows in Mid-Lactation," *British Journal of Nutrition*, vol. 69, pp. 103-115 (1993).

Oldick et al. "Abomasal Infusion of Glucose and Fat-Effect on Digestion, Production, and Ovarian and Uterine Functions of Cows," (abstract), *J. Dairy Sci,.* vol. 80, pp. 1315-1328 (Jul. 1997), published at: <http://www.aces.uiuc.edu/-gregm/adsa/jds/abs/97/Jul97/ab1315.html>.

Istasse et al. "The Effects of Abomasal Infusions of Casein or Glucose on Milk Yield and on Some Blood Constituents of Diary Cows in Early and Late Lactation" (Abstract), *Journal of British Society of Animal Production*, pp. 538-539. (1984).

Oldham et al. "Milk Production in Cows Infused Abomasally with Casein, Glucose or Aspartic and Glutamic Acids Early in Lactation" (Abstract), *Proceedings of the Nutrition Society*, p. 65A, vol. 43 (1984).

Lister et al. "Effects of Intraruminal Administration of Polyol to Sheep," *J. Sci. Food Agric.*, vol. 35, pp. 21-28 (1984).

Sauer et al. "Propylene Glycol and Glycerol as a Feed Additive for Lactating Dairy Cows: An Evaluation of Blood Metabolite Parameters," *Canadian Journal of Animal Science*; vol. 53, pp. 265-271, 1973.

Fisher et al. "Effects of Propylene Glycol or Glycerol Supplementation of the Diet of Dairy Cows on Feed Intake, Milk Yield and Composition, and Incidence of Ketosis," *Canadian Journal of Animal Science*, vol. 53, No. 2; pp. 289-296 (1973).

Boyd et al Effects of the Addition of Direct-FED Microbials & Glycerol to the Diet—J. of Dairy Sci. 94: pp. 4616-4622, Nov. 3, 2010.

Lundeen in Feedstuffs, Jul. 11, 2005 vol. 77 #28 Supplements Aid Dairy Cows.

SYSTEMS AND METHODS FOR FEEDING SUGAR ALCOHOL TO RUMINANTS DURING PERIODS OF HEAT STRESS

CROSS-REFERENCED RELATED APPLICATIONS

This application is a continuation of U.S. patent application Ser. No. 14/727,304 filed on Jun. 1, 2015, issued as U.S. Pat. No. 9,456,622 on Oct. 4, 2016, which is a continuation of U.S. patent application Ser. No. 14/158,209 filed on Jan. 17, 2014, issued as U.S. Pat. No. 9,044,041 on Jun. 2, 2015, which is a continuation of U.S. patent application Ser. No. 13/363,973 filed on Feb. 1, 2012, issued as U.S. Pat. No. 8,658,199 on Feb. 25, 2014, the entire contents of which are incorporated herein by reference.

FIELD OF THE INVENTION

Implementations provide systems and methods for feeding sugar alcohol to ruminants during periods of heat stress to increase performance of the heat stressed ruminant.

BACKGROUND

Heat stress can reduce intake and milk production in lactating dairy cattle. During periods of excessive heat, when environmental temperatures and humidity are high, cooling systems such as combinations of fans, sprinklers, curtains, and natural ventilation systems may be used to cool the ambient air environment and the dairy cattle within the environment or may be used to directly cool the dairy cattle through evaporation of liquid from the skin surface. However, water supplies for cooling the air or for cooling the dairy cattle may be unavailable, and when available, sprinkler systems may drift or may provide inadequate amounts of water for sufficient cooling. Fans may be incorrectly placed for cooling, may fail and require maintenance and the amount of fan cooling may be limited by electrical capacities.

In some cases, heat stressed dairy cattle may be provided more access to drinking water, may be moved to shaded sides of a barn throughout the day or may be penned in small groups or separately penned in order to reduce the effects of heat stress. However, undersized water supply lines may limit access to water, and availability of stalls may be limited, which may prevent the dairy cattle from being moved to shaded areas or to separate or small group pens.

Even with cooling systems, supplemental water, shade or modified pen arrangements, in humid conditions, dairy cattle performance may be negatively impacted and intake and milk production may not reach levels observed during cool, less humid conditions.

SUMMARY

Implementations are directed to systems and methods for feeding sugar alcohol such as sorbitol to ruminants experiencing heat stress or that may become heat stressed, for example, due to high temperatures, humidity, dew points or combinations thereof. Sugar alcohol provided to a ruminant such as a dairy cow during various phases of lactation may improve performance through increased milk yield, improved feed efficiency or both compared to heat stressed ruminant without sorbitol in the diet.

In one implementation, a method of improving ruminant performance during heat stress includes determining a ruminant is experiencing heat stress and feeding the heat stressed ruminant an effective amount of sugar alcohol to improve performance.

In another implementation, a method of feeding lactating dairy cattle sugar alcohol for improving performance during periods of heat stress includes feeding the lactating dairy cattle sugar alcohol in an amount of about 100 grams of sugar alcohol per dairy cattle per day to cause the lactating dairy cattle to increase performance during periods of heat stress.

In another implementation, a feeding system includes a dairy cattle feed mixture comprising sugar alcohol, wherein the dairy cattle feed mixture is provided to a heat stressed dairy cattle in an amount that delivers about 100 grams of sugar alcohol to the heat stressed dairy cattle per day.

DETAILED DESCRIPTION

Figure 1:
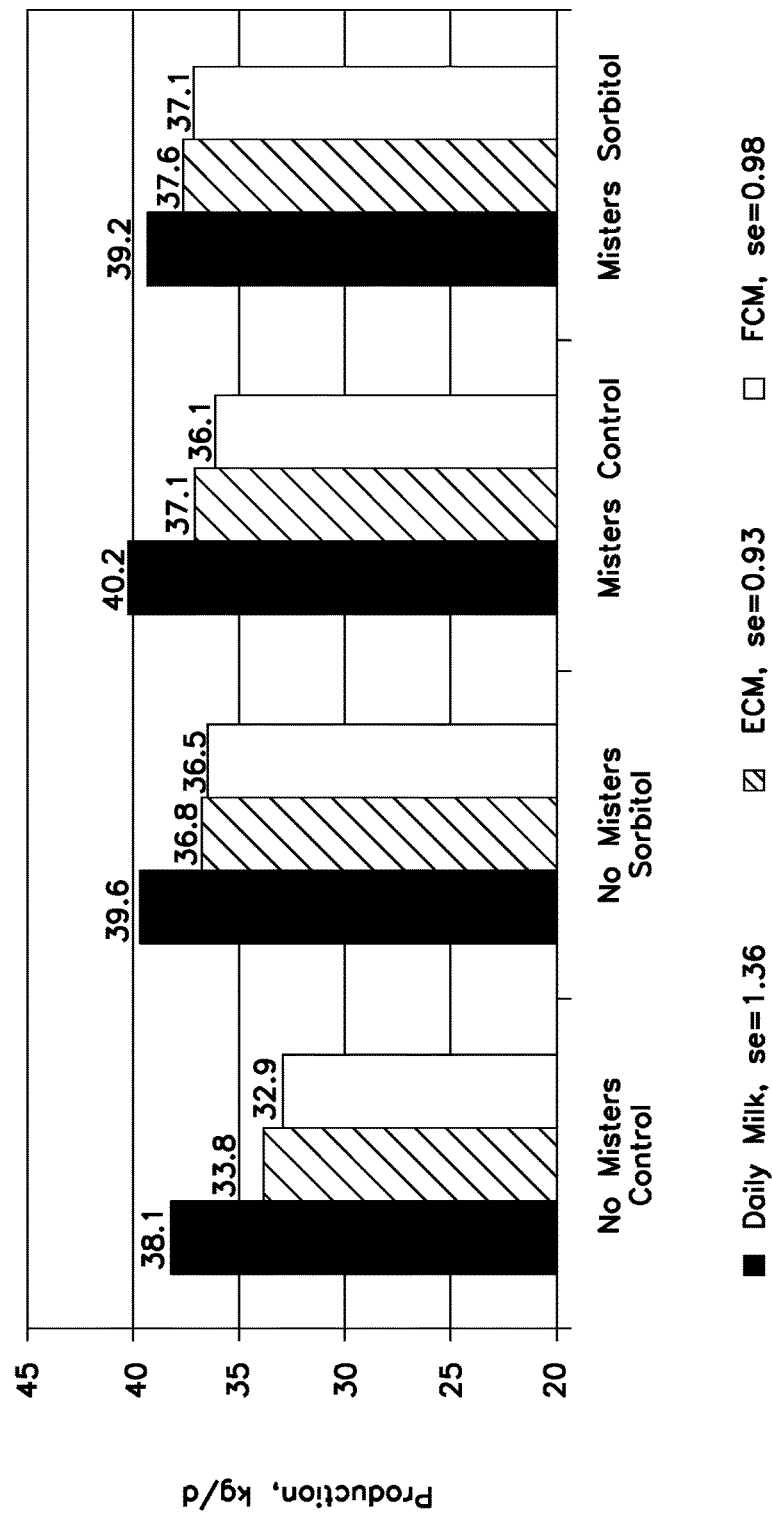
FIG. 1 is a bar chart showing the daily milk, energy corrected milk (ECM) and fat corrected milk (FCM) for the four treatment groups studied for the effect of feeding sorbitol to heat stressed lactating dairy cattle.

Systems and methods provide a sugar alcohols such as sorbitol in the ruminant diet to improve ruminant performance. Improved performance may include improved dry matter intake, milk production (e.g., milk yield and/or milk component yield) or both, during periods of heat stress. The improved performance may be observed during various stages of lactation including transition, mid-lactation and post-peak phases. By consuming sugar alcohols such as sorbitol during periods heat stress, it has been discovered that the ruminants may have greater milk yield or improved feed efficiency compared to heat stressed ruminants not consuming a sugar alcohol. Enhancing milk yield may mean the overall milk yield or milk component yield is enhanced. Such milk components may include but are not limited to enhanced fat content, true protein, lactose and total solids.

According to certain implementations, one or more sugar alcohols may be provided in the ruminants diet in liquid application, may be applied to the feed ration, may be fed, blended or pelleted with grain concentrates, may be provided as extruded pellets, in dry powdered form, as by-product feeds, may be added to the feed ration, and may be provided in combinations and variations thereof.

Sugar alcohols that may be used to improve the performance of heat stressed ruminants may include, but are not limited to, sorbitol; xylitol; glycerol; adonitol; allitol; altritol; arabitol; dulcitol; erythritol; galaxitol; glucitol; iditol; insitol; isomalt; lactiol; malitol; mannitol; perseitol; ribitol; rhamnitol; threitol, D-isomers, L-isomers, and D- and L-isomers thereof. In addition, one or more of the above sugar alcohols may be excluded from the ruminant's diet.

In some implementations, an effective amount of sugar alcohol may be ingested by the ruminant per day. For example, an effective amount of sugar alcohol may be about 70, 75, 80, 85, 90, 95, 100, 105, 110 grams per day, most preferably at about 100 grams per day, or may be provided from about 50 to about 100 grams per day, from about 50 to about 150 grams per day, from about 75 to about 125 grams per day, and from about 80 to about 100 grams per day. The effective amounts of sugar alcohol may, for example, be delivered to the ruminant in a dry pellet form and ingested orally. In a preferred implementation, sorbitol may be provided at about 100 grams per ruminant per day in a dry pellet form.

Along with the sugar alcohol, the diet fed to the ruminant may include other ruminant feed components capable of being blended, mixed or incorporated with sugar alcohol. Generally, the feed components should not degrade the sugar alcohol or decrease the sugar alcohol's effectiveness (e.g., the feed components should not counteract the effects of sugar alcohol). Some feed components that may be incorporated with sugar alcohol in the ruminant may include water, corn silage, legume silages, alfalfa hay, mixed hays (e.g., legumes and grasses) grains (e.g., soybeans, corn, milo), grain mixtures, grain meals, formula feeds, and nutritional supplements (e.g., fatty acids and vitamins). In some implementations, the total diet should be formulated for the stage of lactation and may be approximately 40 to 55 percent concentrates with the remainder being forages (e.g., silages and hays).

According to certain implementations of use, sugar alcohol in the diet may be provided to the ruminant during all or a portion of the year in which the ruminant is challenged by environmental heat stress (e.g., based on historical weather patterns) to improve ruminant performance. Sugar alcohol may also be provided intermittently during the year in anticipation of periods of heat stress (e.g., based on short-term or long-term weather forecasts). In another implementation, the sugar alcohol in the ruminant diet may be fed to the ruminant only during periods of observed heat stress in the ruminant. Heat stress may be observed in the ruminant by one or more of increased respiration rates from about 29 cycles per minute, standing, or about 35 cycles per minute, recumbent, decreased performance (e.g., decreased milk yield), decreased dry matter or feed intakes (e.g., a reduction of approximately 10 percent), elevated internal body temperature, open mouth breathing, excessive panting, sweating, and failed reproduction.

In addition to feeding sugar alcohol to the ruminant, the environment in which the ruminant resides may be cooled to improve ruminant performance. In the environmental cooling method, the facility may be naturally ventilated using curtain sidewalls, which may be thermostatically controlled to be lowered at approximately 55 degrees F. The facility may be open at the center of the roof to allow warm air to escape. A series of fans may be placed over the stalls and one group may thermostatically activate at one temperature, e.g., 60 degrees F., while another group may thermostatically activate at a different temperature, e.g., 66 degrees F. Thus, the curtain sidewalls and groups of fans may operate continuously when the ambient temperature is greater than for example 66 degrees F.

In another implementation for improving ruminant performance, ruminants may be fed sugar alcohol and may be cooled directly by evaporative cooling methods. For example, water may be applied in a limited amount to the ruminant's body (e.g., on the back) and natural ventilation and fans may be used to evaporate the water from the hide. The evaporative cooling method may improve the ability of the ruminant to dissipate internal heat. The water delivery system may include a sprinkler nozzle system (e.g., low-pressure sprinklers) for spraying water onto the bodies of the ruminant. The evaporative cooling method may be used when the ambient temperature is at a first threshold, e.g., greater than 72 degrees F., and the water delivery system may operate intermittently, e.g., for 30 seconds in 7 minute intervals. When the ambient temperature is at a second threshold, e.g., greater than 86 degrees F., the water delivery system may operate longer at more frequent intervals, for 42 seconds in 5.5 minute intervals. In some implementations, the evaporative cooling method may be used in combination with the above-described environmental cooling method.

Heat stressed ruminants consuming sugar alcohol in the diet may improve milk yield and milk component yield, such as by approximately 8-10 percent compared with heat stressed cows not consuming sugar alcohol. In addition, ruminants fed sugar alcohol may be more efficient in the conversion of nutrients for the production of milk.

In some implementations, the amount of sugar alcohol provided to the ruminant, the type of sugar alcohol provided to the ruminant, or both, may change based on lactation phase. For example, in a transition phase, the ruminant may be provided a first amount of sugar alcohol prior to calving and may be provided a second amount of sugar alcohol, different from the first amount, after calving.

In a particular example, a heat stressed ruminant in a transition phase may be provided with 150 grams of sugar alcohol per day, at post-calving may receive 125 grams of sugar alcohol per day and thereafter may receive 100 grams of sugar alcohol per day. The 125 gram amount may be provided post-calving for example from days 1 to 14, days 1 to 100, days 14 to 100, days 1 to 200, days 14 to 200 or days 100 to 200 post-calving. The 100 gram amount may be provided to the heat stressed ruminant during lactation for example from days 14 to 100, days 14 to 200, days 14 to 305, days 100 to 200, days 100 to 305 or days 200 to 305.

In another example, the ruminant may be provided different amounts or types of sugar alcohol as the ruminant transitions from the early lactation phase (e.g., days 14 to 100) to the mid-lactation phase (e.g., days 100 to 200), from the mid-lactation phase to the late lactation phase (e.g., days 200 to 305), or both.

In some implementations, the ruminant may be provided the same or varying amounts of one or more sugar alcohols but the type of improvement in performance during periods of heat stress may change over time. For example, providing a sugar alcohol to a ruminant in a transition phase may improve milk yield, while providing the sugar alcohol to the ruminant upon reaching mid-lactation may improve dry matter intake.

Adding sugar alcohol to the diets of heat stressed ruminant may cause the metabolism to spare glucose for the mammary gland, may alter liver metabolism to increase glucose, may act as an alternative of glucose for peripheral tissues metabolism, may affect endocrine control of metabolism to spare glucose, or combinations thereof.

Implementations may be applicable to a number of ruminants including dairy cattle and other even-toed hoofed animals having a three- or four-chamber stomach. Ruminants may be animals that re-chew stomach contents. Such ruminants include but are not limited to alpacas; antelopes; bison; camels; deer; giraffes; goats; guanicos; llamas; musk oxen; oxen; and sheep.

These and other advantages may be appreciated in the following Examples, which are intended to be illustrative, and numerous modifications and variations may be implemented in view of the present disclosure, which may be apparent to those skilled in the art.

In the Examples below, statistical analysis was completed for parameters studied such as milk yield, energy corrected milk (ECM), fat corrected milk (FCM), and dry matter intake. A P value of 0.10 means that 10 times out of 100 the results can be explained by factors other than the feeding of sorbitol versus the lack of sorbitol feeding. Likewise, a P value of 0.75 means that 75 times out of 100, the difference in value between the control group and the sorbitol-fed group may be explained by factors other than the feeding of the increased rate(s) of supplemental feed versus the lower rate of feeding of the supplemental feed (e.g., 4 pounds per head per day). For purposes of comparing data in this document, P values of 0.15, or lower, are considered statistically significant. Thus, where a P value of 0.15 or less is returned for particular results, it is assumed that the differing results may be explained by the test regimen, i.e.: the feeding of the increased rate(s) of supplemental feed versus the lower rate of feeding of the supplemental feed (e.g., 4 pounds per head per day).

Example 1

This example demonstrates the effect of feeding heat stressed lactating dairy cattle in a post-peak phase of lactation about 100 grams of sorbitol per day, with and without an evaporative cooling system. In this example, 32 multiparous cows were blocked by production and days in milk into one of two diets, a control diet without sorbitol and a diet with sorbitol, and each treatment group was divided into two cooling treatments. The four treatment groups included 1) a control diet with fans and no mist; 2) a sorbitol-supplemented diet with fans and no mist; 3) a control diet with fans and mist; and 4) a sorbitol-supplemented diet with fans and mist. During the study, the ambient temperature was between 70 degrees and 85 degrees during 51 percent of study and was greater than 85 degrees during 13 percent of the study. Heat stress in the dairy cattle was observed through changes in performance as well as increased respiration rates. Dairy cattle performance and respiration rates for the dairy cattle not receiving mister cooling is compared to dairy cattle receiving mist treatment in Table 1.

TABLE 1

|  | Misters | No Misters | P-value |
| --- | --- | --- | --- |
| Daily Milk, kg/d | 39.7 | 38.9 | ns |
| ECM, kg/d | 37.4 | 35.3 | 0.02 |
| FCM, kg/d | 36.6 | 34.7 | 0.05 |
| DMI, kg/d | 26.1 | 25.0 | ns |
| Fat, % | 3.11 | 3.01 | ns |
| Fat, kg/d | 1.20 | 1.13 | 0.05 |
| Protein, % | 2.94 | 2.87 | 0.06 |
| Protein, kg/d | 1.16 | 1.08 | 0.05 |
| Milk to Feed | 1.56 | 1.57 | ns |
| Respiration rates | 60.08 | 65.7 | 0.08 |

The sorbitol in the sorbitol-supplemented diets was processed as an extruded pellet and added to other grain concentrates prior to final addition and delivery to the ruminant.

The components of the control ration and the sorbitol ration are shown in Table 2:

TABLE 2

| Ingredients: pounds of DM | Control | Sorbitol |
| --- | --- | --- |
| Corn Silage | 16.5 | 16.5 |
| Alfalfa Hay (48.5% Forage DM) | 9.0 | 9.0 |

TABLE 2-continued

| Ingredients: pounds of DM | Control | Sorbitol |
| --- | --- | --- |
| Base Grain Mix | 17.17 | 17.17 |
| Control Mix | 9.83 | 0 |
| Sorbitol Treatment Mix | 0 | 9.83 |
| Total | 52.5 | 52.5 |

The nutrient analysis of the total mixed ration are shown in Table 3:

TABLE 3

|  | Control | Sorbitol |
| --- | --- | --- |
| CP, % | 17.4 | 17.7 |
| ADF, % | 18.7 | 18.7 |
| NDF, % | 28.4 | 28.8 |
| Fat, % | 4.5 | 4.5 |
| Starch, % | 22.4 | 21.5 |
| Forage NDF, % | 19.6 | 19.6 |
| MP, % | 11.6 | 11.7 |
| ME, Mcal/lb | 1.32 | 1.32 |

The effects of feeding sorbitol to heat stressed dairy cattle is shown in Table 4:

TABLE 4

|  | Control | Sorbitol | P-value |
| --- | --- | --- | --- |
| Daily Milk, kg/d | 39.2 | 39.4 | ns |
| ECM, kg/d | 35.4 | 37.2 | 0.05 |
| FCM, kg/d | 34.5 | 36.8 | 0.02 |
| DMI, kg/d | 26.4 | 24.7 | 0.07 |
| Fat, % | 2.96 | 3.16 | ns |
| Fat, kg/d | 1.11 | 1.23 | 0.03 |
| Protein, % | 2.93 | 2.87 | 0.09 |
| Protein, kg/d | 1.12 | 1.12 | ns |
| Milk to Feed | 1.48 | 1.60 | 0.01 |
| Respiration rates | 62.8 | 63.0 | ns |

Control and Sorbitol were pooled across cooling strategies and day

The results of Table 4 illustrate that feeding sorbitol to heat stressed dairy cattle positively affects milk yield and milk component yield, reduces dry matter intake, and improves milk-to-feed ratios, described further below.

FIG. 1 shows a bar chart of the daily milk, energy corrected milk (ECM) and fat corrected milk (FCM) for the four treatment groups in the study. In each group receiving sorbitol, dairy cattle performance was improved over the performance of the control groups. Daily milk yield, FCM and ECM was lowest for the control group without misters and without sorbitol in the diet, as expected. Dairy cattle receiving sorbitol and mister treatment had the best overall performance in comparison to all other groups studied, and the group with sorbitol and without mister treatment performed better than the control group without misters in all performance areas. ECM and FCM yield improved for both the sorbitol groups compared to their counterpart control groups.

With respect to daily milk yield results, the control group with misters having the highest milk yield may be due to increased dry matter intake. This may be evidenced by the sorbitol and mister group having comparatively higher ECM and FCM performance.

With respect to the ECM results, heat stressed dairy cattle receiving sorbitol without mister treatment performed significantly better than the control group without sorbitol and mister treatment. In addition, the sorbitol group without mister treatment performed similarly to the control group with misters, with 0.3 kg/d difference in ECM. Thus, heat stressed dairy cattle receiving sorbitol may perform substantially equally compared to heat stressed dairy cattle undergoing evaporative cooling methods such as misters.

With respect to the FCM results, heat stressed dairy cattle receiving sorbitol with and without mister treatment performed better than the control group with mister treatment and significantly better than the control group without mister treatment.

Figure 2:
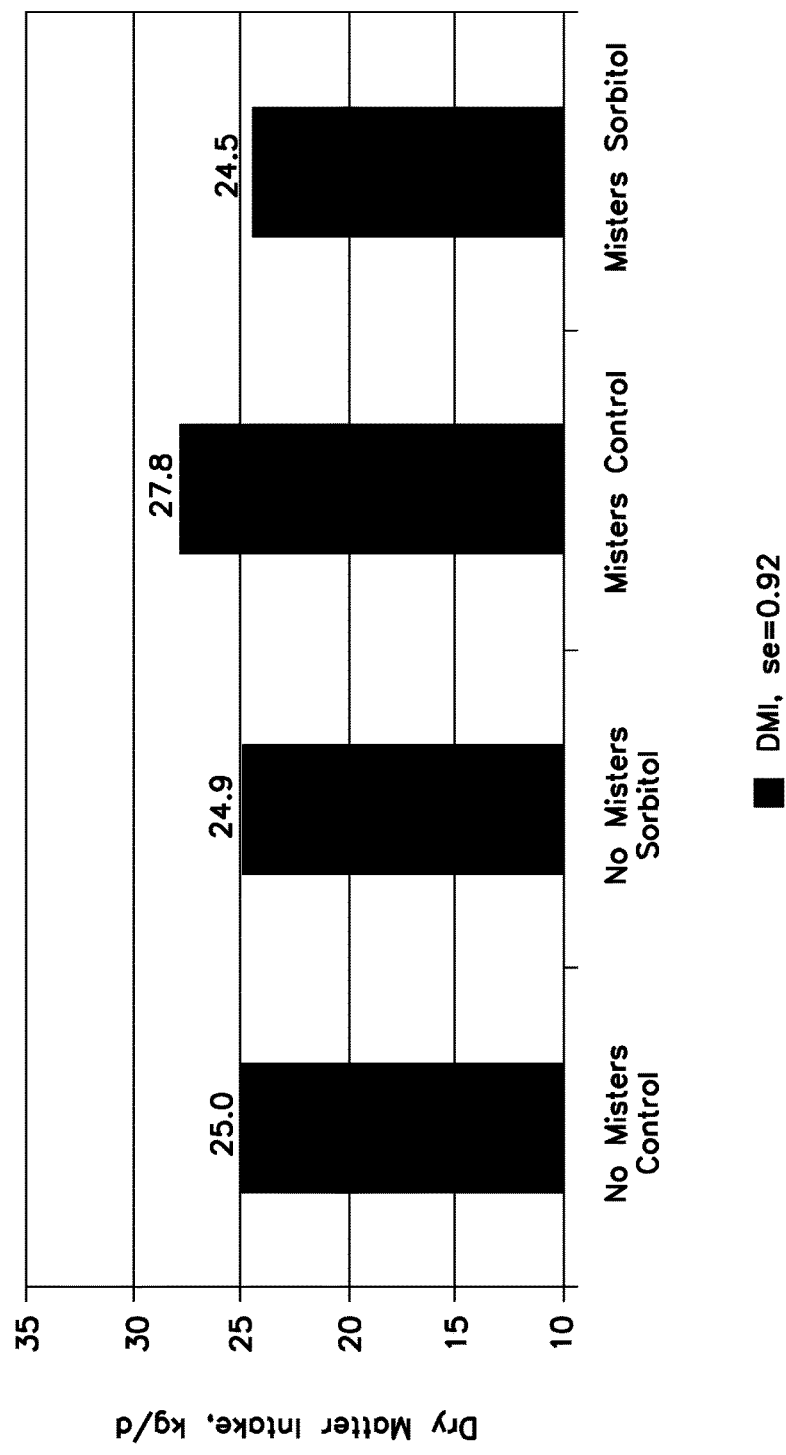
FIG. 2 is a bar chart showing the daily dry matter intake in kilograms per day for each of the four treatment groups studied.
Figure 3:
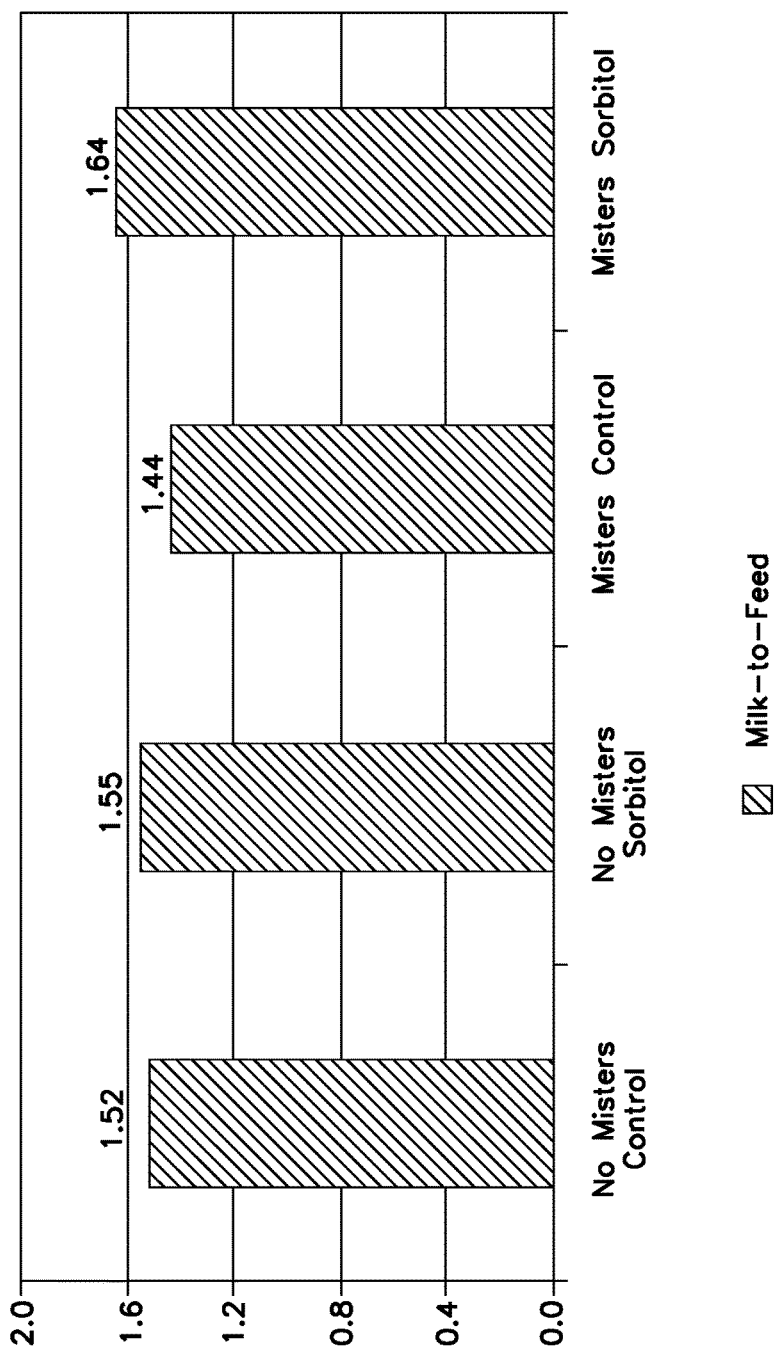
FIG. 3 is a chart showing milk-to-feed ratio for each of the four treatment groups studied.

FIG. 2 shows a bar chart of the daily dry matter intake in kilograms per day for each of four treatment groups studied. The dry matter intake was greatest at 28 kg/day for the control group with mister treatment compared to 25 kg/day for the other groups. Dry matter intake for the two sorbitol groups varied by 0.4 kg/d. As a result of the differences in the dry matter intake for the control group with mister treatment compared to the sorbitol groups, the milk-to-feed ratio was highest for the sorbitol groups, e.g., feed efficiency was highest for the sorbitol groups. Particularly as shown in the graph of FIG. 3, for every kg of dry matter consumed for the control group with misters, 1.44 kg of milk was produced, whereas the sorbitol group without mister treatment produced 1.55 kg of milk for every kg of dry matter consumed, and the sorbitol group with mister treatment produced 1.64 kg of milk for every kg of dry matter consumed. With respect to the control group without misters, the milk-to-feed ratio was 1.52, thus indicating that the performance of the sorbitol groups without and with mister treatment was improved at 1.55 and 1.64, respectively. Accordingly, adding sorbitol to the diets of lactating dairy cattle during periods of heat stress when dry matter intake is reduced improves performance including milk yield, milk component yield and feed efficiency.

Example 2

This example demonstrates the effects of feeding 64 heat stressed transition dairy cattle (e.g., in a prefresh stage and a postfresh stage up to 60 days after calving) receiving about 150 grams of sorbitol per day prior to calving and about 125 grams of sorbitol per day, with and without an evaporative cooling system. In this example, the dairy cattle were blocked in the same manner as Example 1. During the study, the ambient temperature was between 70 degrees and 85 degrees during 62 percent of study and was greater than 85 degrees during 18 percent of the study. Heat stress was observed in the dairy cattle in a manner similar to Example 1.

Table 5A illustrates the different treatment groups and dietary components of the diets of the treatment groups.

TABLE 5A

| N = 60 | | Prefresh days 28 to 0 | Postfresh Days 0 to 30 | Days 31 to 60 |
|---|---|---|---|---|
| Control | No Misters | Control | Control | High |
| Sorbitol | No Misters | 1.5 lb/d base mix | 1.25 lb/d base mix | High |
| Control | Misters | Control | Control | High |
| Sorbitol | Misters | 1.5 lb/d base mix | 1.25 lb/d base mix | High |

The control and sorbitol diets for the prefresh and postfresh cows were composed of substantially the feed components provided in Table 5B.

TABLE 5B

| Ingredients: pounds of DM | Prefresh Control | Prefresh Sorbitol | Postfresh Control | Postfresh Sorbitol |
|---|---|---|---|---|
| Corn Silage | 11.0 | 11.0 | 18.0 | 18.0 |
| Grass Hay | 4.5 | 4.5 | | |
| Alfalfa Hay | | | 8.5 | 8.5 |
| Base Grain Mix | 10.17 | 10.17 | 16 | 16 |
| High Org | | | 7.75 | 7.75 |
| Control Mix | 1.5 | | 1.25 | |
| Sorbitol Treatment Mix | | 1.5 | | 1.25 |
| Total | 27.17 | 27.17 | 51.5 | 51.5 |

After 30 days in milk, all postfresh cows were fed a common diet until 60 days post partum. The nutrient analysis of the total mixed rations for the control and sorbitol diets provided during the study are shown in Table 5C:

TABLE 5C

| | Prefresh Control | Prefresh Sorbitol | Postfresh Control | Postfresh Sorbitol |
|---|---|---|---|---|
| CP, % | 15.1 | 15.1 | 16.8 | 16.8 |
| ADF, % | 25.4 | 24.7 | 19.7 | 19.5 |
| NDF, % | 39.7 | 39.1 | 31.2 | 30.9 |
| Fat, % | 2.7 | 2.7 | 5.0 | 5.0 |
| Starch, % | 23.5 | 24.7 | 26.2 | 26.7 |
| Forage NDF, % | 26.4 | 26.4 | 20.9 | 20.9 |
| MP, % | 10.6 | 10.7 | 11.9 | 11.9 |
| ME, Mcal/lb | 1.2 | 1.2 | 1.3 | 1.3 |

As provided in FIGS. 5A and 5B, sorbitol was provided in a base mix at a rate of 1.5 pounds per day for prefresh dairy cattle (e.g., for 28 days prior to calving) and at a rate of 1.25 pounds per day for post fresh dairy cattle (e.g., for 30 days post-calving).

The effects of feeding sorbitol to heat stressed dairy cattle after 30 days from calving is shown in Table 6A.

TABLE 6A

| day 0 to 30 postpartum | | Control No Misters | Sorbitol No Misters | Control Misters | Sorbitol Misters | SE | Diet* Cooling P-Value |
|---|---|---|---|---|---|---|---|
| Daily Milk Yield | lbs/d | 67.2 | 74.4 | 81.1 | 78.7 | 2.17 | 0.03 |
| Dry Matter Intake | lbs/d | 33.4 | 36.8 | 38.1 | 37.8 | 1.24 | 0.14 |
| Body Weight, post | lbs | 1222 | 1232 | 1303 | 1259 | 31.71 | ns |
| DMI as % BW | % | 2.78 | 3.03 | 3.01 | 3.05 | 0.09 | ns |
| ECM | lbs/d | 74.9 | 75.2 | 82.2 | 80.2 | 2.32 | ns |
| FCM | lbs/d | 75.9 | 75.5 | 81.9 | 80.7 | 2.39 | ns |
| Milk Fat | % | 3.85 | 3.42 | 3.65 | 3.53 | 0.12 | 0.18 |
| Milk Protein | % | 2.88 | 2.81 | 2.89 | 2.81 | 0.05 | ns |
| Milk-to-Feed Ratio | | 2.11 | 2.05 | 2.11 | 2.08 | 0.04 | ns |

The results of Table 6A show the groups ingesting sorbitol performed better than the control group not receiving mister treatment. For example, the sorbitol treatment group without mister treatment increased milk yield by about 7.2 pounds per day and the sorbitol and mister treatment group increased milk yield by about 11.5 pounds per day (or increased by between about 11 percent and about 17 percent) compared to the control group without mister treatment. Dry matter intake increased by between about 3.4 to about 4.4 pounds per day (or increased by between about 10 percent and about 13 percent) compared to the control group without mister treatment. P* diet cooling values indicate the response or magnitude of the response to cooling was also influenced by the diet. The four treatments were influenced differently as to the main effect of either cooling or diet, and for the P* diet cooling values listed, the interaction between the diet parameter and cooling was measurable.

The effects of feeding sorbitol to heat stressed dairy cattle after 60 days from calving is shown in Table 6B. From day 30 to day 60, all dairy cattle study groups received the same diet free of sorbitol (see Table 5).

TABLE 6B

| day 0 to 60 postpartum | | Control No Misters | Sorbitol No Misters | Control Misters | Sorbitol Misters | SE | Diet* Cooling P-Value |
|---|---|---|---|---|---|---|---|
| Daily Milk Yield | lbs/d | 73.0 | 81.2 | 86.6 | 84.3 | 1.54 | 0.01 |
| Dry Matter Intake | lbs/d | 39.1 | 41.1 | 43.4 | 42.9 | 0.87 | 0.16 |
| Body Weight, post | lbs | 1220 | 1231 | 1299 | 1261 | 28.16 | ns |
| DMI as % BW | % | 3.25 | 3.32 | 3.48 | 3.45 | 0.06 | ns |
| ECM | lbs/d | 76.7 | 77.3 | 82.2 | 79.8 | 1.94 | ns |
| FCM | lbs/d | 77.7 | 77.7 | 82.4 | 80.4 | 2.07 | ns |
| Milk Fat | % | 3.48 | 3.12 | 3.32 | 3.17 | 0.08 | 0.15 |
| Milk Protein | % | 2.72 | 2.66 | 2.72 | 2.66 | 0.04 | ns |
| Milk-to-Feed | | 1.94 | 1.97 | 1.98 | 2.00 | 0.03 | ns |

In Table 6B, the groups ingesting sorbitol for 28 days pre-partum and 30 days postpartum after 60 days performed better than the control group not receiving mister treatment. For example, the sorbitol treatment group without mister treatment increased milk yield by about 8.2 pounds per day and the sorbitol and mister treatment group increased milk yield by about 11.3 pounds per day (or increased by between about 11 percent and about 15.5 percent) compared to the control group without mister treatment. Dry matter intake increased by between about 2 to about 3.8 pounds per day (or increased by between about 5 percent and about 10 percent) compared to the control group without mister treatment. In addition, milk-to-feed ratios increased to 1.97 and 2.0 for the sorbitol treatment groups compared to the control group without mister treatment at 1.94. For the two mister treatment groups, the sorbitol group increased its milk-to-feed ratio to 2.0 compared to the control group at 1.98.

Figure 4:
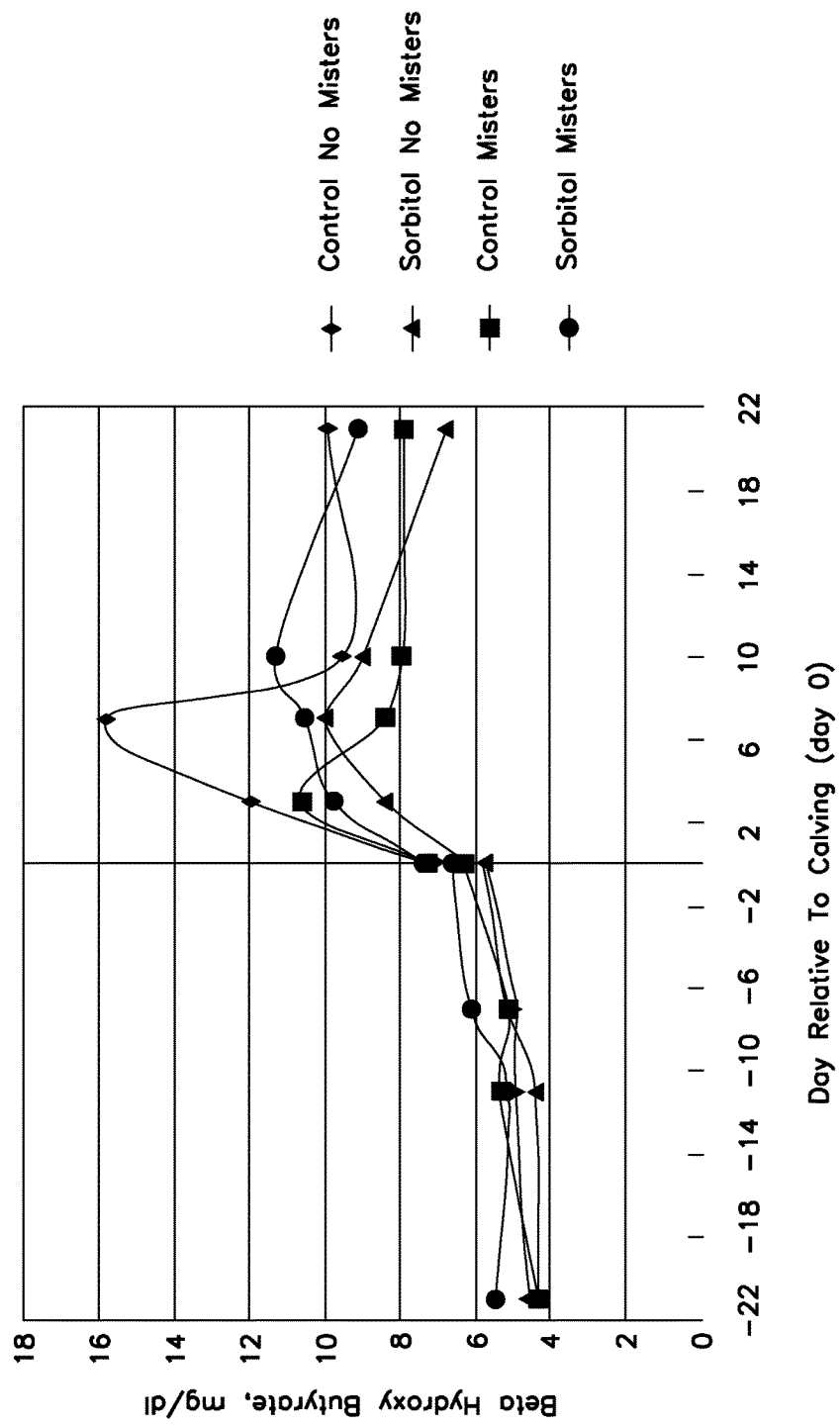
FIG. 4 provides a graph illustrating beta hydroxy butyrate (BHBA) levels for the four treatment groups studied during the transition phase.

Providing sorbitol in the diets of the transition dairy cattle may reduce beta hydroxyl butyrate (BHBA) levels, and therefore may help prevent or reduce the incidence of ketosis or fatty liver syndrome in the dairy cattle. FIG. 4 provides a graph illustrating BHBA levels in the transition dairy cattle in the four groups studied and shows the control group without mister treatment experienced a spike in BHBA levels compared to the sorbitol groups.

Example 3

This example demonstrates the effects of feeding sorbitol to dairy cattle in mid-lactation (e.g., about 100 to about 200 days in milk) at a rate of about 100 grams per day. 64 dairy cattle were separated into four pens of 16 dairy cattle each pen was provided one of the four treatments described above in connection with Example 1. The treatment groups receiving sorbitol in the diet were provided 1 pound of premix per day during a ten week testing period. During the study, the temperature was between 70 degrees and 85 degrees during 82 percent of study and was greater than 85 degrees during 25 percent of the study. Heat stress was observed in the dairy cattle in a manner similar to Example 1.

The control and sorbitol diets for the prefresh and postfresh cows were composed of substantially the feed components provided in Table 7A.

TABLE 7A

| Ingredients: pounds of DM | Control | Sorbitol |
|---|---|---|
| Corn Silage | 14.0 | 14.0 |
| Alfalfa Hay | 11.5 | 11.5 |
| Grass Hay | 1.5 | 1.5 |
| Base Grain Mix | 16.0 | 16.0 |
| High Org | 8.0 | 8.0 |
| Control Mix | 1.0 | |
| Sorbitol Treatment Mix | | 1.0 |
| Total | 52.0 | 52.0 |

The nutrient analysis of the total mixed rations for the control and sorbitol diets provided during the study are shown in Table 7B:

TABLE 7B

| | Control | Sorbitol |
|---|---|---|
| CP, % | 17.3 | 17.3 |
| ADF, % | 20.7 | 20.5 |
| NDF, % | 32.0 | 31.7 |
| Fat, % | 4.9 | 4.9 |
| Starch, % | 23.5 | 24.7 |
| Forage NDF, % | 24.3 | 24.7 |
| MP, % | 12.0 | 12.0 |
| ME, Mcal/lb | 1.3 | 1.3 |

Table 8 illustrates the effects of feeding sorbitol in the diet of dairy cattle in mid-lactation.

TABLE 8

| | Control No Misters | Sorbitol No Misters | Control Misters | Sorbitol Misters | SE | Diet * Cooling, P-value |
|---|---|---|---|---|---|---|
| Dry Matter Intake, lbs/d | 48.8 | 51.2 | 52.0 | 49.4 | 0.6 | 0.0001 |
| Daily Milk Yield, lbs/d | 70.2 | 71.9 | 73.6 | 73.7 | 1.1 | ns |
| Body Weight, lbs | 1353 | 1393 | 1367 | 1373 | 6.8 | 0.01 |
| ECM, lbs/d | 65.5 | 67.3 | 69.0 | 68.1 | 1.9 | ns |
| 3.5% FCM, lbs/d | 64.2 | 66.0 | 67.9 | 66.7 | 2.1 | ns |
| Milk Fat, % | 3.00 | 3.03 | 2.97 | 2.92 | 0.07 | ns |
| Milk Protein, % | 2.91 | 2.92 | 2.87 | 2.92 | 0.03 | ns |

The results of Table 8 illustrate that the groups ingesting sorbitol during mid-lactation performed better than the control group not receiving mister treatment. For example, the sorbitol treatment group without mister treatment increased milk yield by about 1.7 pounds per day and the sorbitol and mister treatment group increased milk yield by about 3.5 pounds per day (or increased by between about 2.5 percent and about 5 percent). Dry matter intake increased by between about 0.6 to about 2.4 pounds per day (or increased by between about 1.2 percent and about 5 percent) compared to the control group without mister treatment.

Although the present disclosure provides references to preferred embodiments, persons skilled in the art will recognize that changes may be made in form and detail without departing from the spirit and scope of the invention.

What is claimed is:

1. A method of feeding a transition ruminant during a transition phase defined by a period during which the ruminant is pregnant and extending through calving by the ruminant, the method comprising:
    during pregnancy, feeding the transition ruminant a diet comprising sugar alcohol in view of a potential for the transition ruminant to experience heat stress, wherein the potential for heat stress is one or more of historical weather patterns, short-term weather forecasts or observed temperature conditions of at least 70° F.; and
    determining the transition ruminant is experiencing heat stress by observing one or more of elevated internal body temperature, open mouth breathing, increased panting, or sweating,
    wherein the sugar alcohol is ingested in an amount in the diet effective to improve performance after calving, wherein the improved performance comprises one or more of increased milk production, increased dry matter intake, increased weight gain, or an improved milk-to-feed ratio, and
    wherein the sugar alcohol comprises at least one of sorbitol, xylitol, adonitol, allitol, altritol, arabitol, dulcitol, erythritol, galactitol, glucitol, iditol, inositol, isomalt, lactitol, maltitol, mannitol, perseitol, ribitol, rhamnitol or threitol.

2. The method of claim 1, further comprising one or more of:
    cooling an environment in which the heat stressed transition ruminant resides, or
    cooling the heat stressed transition ruminant using an evaporative cooling method.

3. The method of claim 2, wherein the improved performance comprises an improved milk-to-feed ratio.

4. The method of claim 1, wherein the sugar alcohol is sorbitol.

5. A method of feeding a lactating ruminant, the method comprising:
    during a period of ambient temperature conditions of at least 70° F., determining the lactating ruminant is experiencing heat stress by observing one of an about 10 percent decrease in dry matter intake, reduced milk production, increased respirations, elevated internal body temperature, open mouth breathing, increased panting, sweating or failed reproduction; and
    feeding the heat stressed lactating ruminant a diet comprising an amount of sugar alcohol effective to improve performance, wherein the improved performance comprises one or more of increased milk production, increased dry matter intake, increased weight gain, or an improved milk-to-feed ratio,
    wherein the sugar alcohol comprises at least one of sorbitol, xylitol, adonitol, allitol, altritol, arabitol, dulcitol, erythritol, galactitol, glucitol, iditol, inositol, isomalt, lactitol, maltitol, mannitol, perseitol, ribitol, rhamnitol or threitol.

6. The method of claim 5, wherein the heat stressed lactating ruminant is a heat stressed mid-lactation phase ruminant defined by a period of about 100 to about 200 days in milk.

7. The method of claim 6, further comprising one or more of:
    cooling an environment in which the heat stressed mid-lactation phase ruminant resides, or
    cooling the heat stressed mid-lactation phase ruminant using an evaporative cooling method.

8. The method of claim 5, wherein the heat stressed lactating ruminant is a heat stressed post-peak phase ruminant.

9. The method of claim 5, wherein the sugar alcohol is sorbitol.

* * * * *